United States Patent
Park et al.

(10) Patent No.: US 6,653,108 B2
(45) Date of Patent: Nov. 25, 2003

(54) PROCESS FOR SELECTIVE AMPLIFICATION OF A FULL-LENGTH CDNA INVOLVING AN ANCHOR NUCLEIC ACID

(75) Inventors: Han-Oh Park, Chungbuk (KR); Jin-Tae Jeon, Chungbuk (KR); Mi-Sook Jang, Chungbuk (KR)

(73) Assignee: Bioneer Corporation, Chungbuk (KR)

(*) Notice: Subject to any disclaimer, the term of this patent is extended or adjusted under 35 U.S.C. 154(b) by 0 days.

(21) Appl. No.: 09/989,706

(22) Filed: Nov. 21, 2001

(65) Prior Publication Data

US 2003/0049637 A1 Mar. 13, 2003

(30) Foreign Application Priority Data

Apr. 27, 2001 (KR) .................. 10-2001-0022956

(51) Int. Cl.[7] ............................ C12Q 1/68; C12P 19/34
(52) U.S. Cl. .................. 435/91.2; 435/6; 435/91.51; 435/91.52
(58) Field of Search .................. 435/6, 91.2, 91.51, 435/91.52

(56) References Cited

U.S. PATENT DOCUMENTS

| | | |
|---|---|---|
| 5,219,989 A | 6/1993 | Sonenberg et al. .......... 530/350 |
| 5,597,713 A | 1/1997 | Kato et al. ................ 435/91.41 |
| 5,659,025 A | 8/1997 | Engels et al. ............... 536/23.1 |
| 5,962,272 A | 10/1999 | Chenchik et al. ........... 435/91.1 |

OTHER PUBLICATIONS

A. Troutt et al., "Ligation–anchored PCR: a simple amplification technique with single–sided specifity," *Proc. Natl. Acad. Sci. USA*, vol. 89, pp. 9823–9825, Oct. 1992.

K. Maruyama et al., Oligo–capping: a simple method to replace the cap structure of eukaryotic mRNAs with Oligoribonucleotides, *Gene*, vol. 138, pp. 171–174, Elsevier Science B.V., 1994.

W. Schmidt et al., "CapSelect: A Highly sensitive method for 5' CAP–dependent enrichment of full–length cDNA in PRC–mediated analysis of mRNAs," *Nucleic Acids Research*, vol. 27, No. 21, pp. i–iv, Oxford University Press, 1999.

*Primary Examiner*—Ethan Whisenant
*Assistant Examiner*—Joyce Tung
(74) *Attorney, Agent, or Firm*—Foley & Lardner

(57) ABSTRACT

The present invention relates to a process for the preparation of full-length complementary DNA (cDNA). More particularly, the present invention is directed to a process for selective amplification of full-length cDNA, which comprises: i) a step for preparing a hybrid composed of a messenger RNA (mRNA) strand and a cDNA strand of which three (3) or four (4) deoxycitidinemono phosphate (dCMP) are combined at 3' end, by treating mRNA with reverse transcriptase; separately from the above step, ii) a step for adenylating single strand anchor of which biotin or phosphate group is combined at 3' end, and phosphate group is combined at 5' end; iii) a step for ligating said adenylated single strand anchor to 3' end of full-length cDNA strand of said cDNA/mRNA hybrid to select full-length cDNA/mRNA hybrid; and iv) a step for amplifying only the full-length cDNA/mRNA hybrid through polymerase chain reaction (PCR) which employs a primer of which base sequence is complementary to that of said anchor.

16 Claims, 4 Drawing Sheets

PROCESS FOR SELECTIVE AMPLIFICATION OF A FULL-LENGTH CDNA INVOLVING AN ANCHOR NUCLEIC ACID

TECHNICAL FIELD

The present invention relates to a process for the preparation of full-length complementary DNA (cDNA). More particularly, the present invention is directed to a process for selective amplification of full-length cDNA, which comprises: i) a step for preparing a hybrid composed of a messenger RNA (mRNA) strand and a cDNA strand of which three (3) or four (4) deoxycitidinemono phosphate (dCMP) are combined at 3' end, by treating mRNA with reverse transcriptase; separately from the above step, ii) a step for adenylating single strand anchor of which biotin or phosphate group is combined at 3' end, and phosphate group is combined at 5' end; iii) a step for ligating said adenylated single strand anchor to 3' end of full-length cDNA strand of said cDNA/mRNA hybrid to select full-length cDNA/mRNA hybrid; and iv) a step for amplifying only the full-length cDNA/mRNA hybrid through polymerase chain reaction (PCR) which employs a primer of which base sequence is complementary to that of said anchor.

BACKGROUND ART

Recently, new techniques for mass production of various genetic engineering products such as proteins, have been developed through identification of novel genes and determination of base sequences thereof, and then characterization of their biological properties.

In addition, some methods for the treatment of various diseases caused by inappropriate expression and/or suppression of a specific gene or by the influence of foreign substance such as carcinogen or teratogen, can be developed through the analysis of the base sequences of the gene.

To these ends, a process for the mass-production of protein having significant biological application, wherein cDNA prepared from mRNA through reverse transcription is inserted into a cloning vector to be cloned, have been developed as a basic skill in biotechnology.

Therefore, the development of more efficient and simple process for the production of full-length cDNA in large scale, have been needed for the mass-production of human cDNA library and for the study of gene expression pattern by using DNA chip.

As a prerequisite tool for the research of expression pattern of human genes and the structure of protein prepared therefrom, the method of 5', 3' end rapid amplification of cDNA end (RACE) is used widely, and the method for determination of complete base sequence by combining those of expressed sequence tags (ESTs) obtained by partial amplification of cDNA, has been developed.

To the present, the method for the preparation of full-length cDNA wherein the cap structure of mRNA is used as a identification marker of full-length cDNA, has been developed. The cap structure of mRNA is characteristic part of the 5' end of eukaryotic mRNA, and contains guanidine nucleotide substituted with methyl group. In general, the cap structure of mRNA is the site recognized by initiation factor in protein synthesis process.

At present, several methods for recognizing the cap structure of the eukaryotic mRNA, for example, a method wherein a fusion protein composed of cap binding protein and solid support matrix, is bound on 5'cap site; a method wherein biotin which can recognize diol group of cap structure, is employed; a method wherein 5'cap structure of mRNA is removed by using tobacco acid pyrophosphatase and then synthetic oligonucleotide is ligated thereto, and etc., are used frequently.

However, these methods are not cost-efficient process and moreover, these methods are time-consuming process because the enzyme treatment step and purification step requires a long time and are so complicated that starting materials may be decomposed or lost during these steps.

Therefore, recently, other methods so called "CapFinder" method or "CapSelect" method are used as a typical method for identification of the cap structure of 5' end of the eukaryotic mRNA during the reverse transcription. However, it takes a long time to add nucleotide on the cap structure of mRNA by employing reverse transcriptase in the CapFinder method, and in addition, the incomplete amplification pattern may be occurred since reverse transcriptase have to recognize template switching oligonucleotide.

The "Capselect" method overcomes partly the above problems. However, "Capselect" method also has drawbacks that it requires an additional step wherein adenine group is added through Ribo-tailing step by using terminal deoxyribonucleotidyl tranferase, and that it requires a step wherein double strand adaptor is linked again. Therefore, "Capselect" method is inappropriate to be employed as a commercial method for the production of full-length cDNA in large scale since it needs considerable time, at least more than ten hours to link double-strand anchor.

Therefore, a novel process by which full-length cDNA can be obtained through more efficient and simple procedures than before, and by which full-length cDNA can be amplified completely to produce full-length cDNA in large scale, has been anticipated in this field.

The purpose of the present invention, therefore, is to provide a novel process to produce full-length cDNA in large scale, comprising a step for obtaining full-length cDNA through only two procedures, reverse transcription of mRNA to obtain cDNA and ligation of anchor and nucleic acid; and a step for amplifying completely the full-length cDNA thus obtained.

BRIEF DESCRIPTION OF THE DRAWINGS

The above objects and other advantages of the present invention will become more apparent by describing in detail the examples thereof with reference to the attached drawings, in which.

DISCLOSURE OF INVENTION

Figure 1:
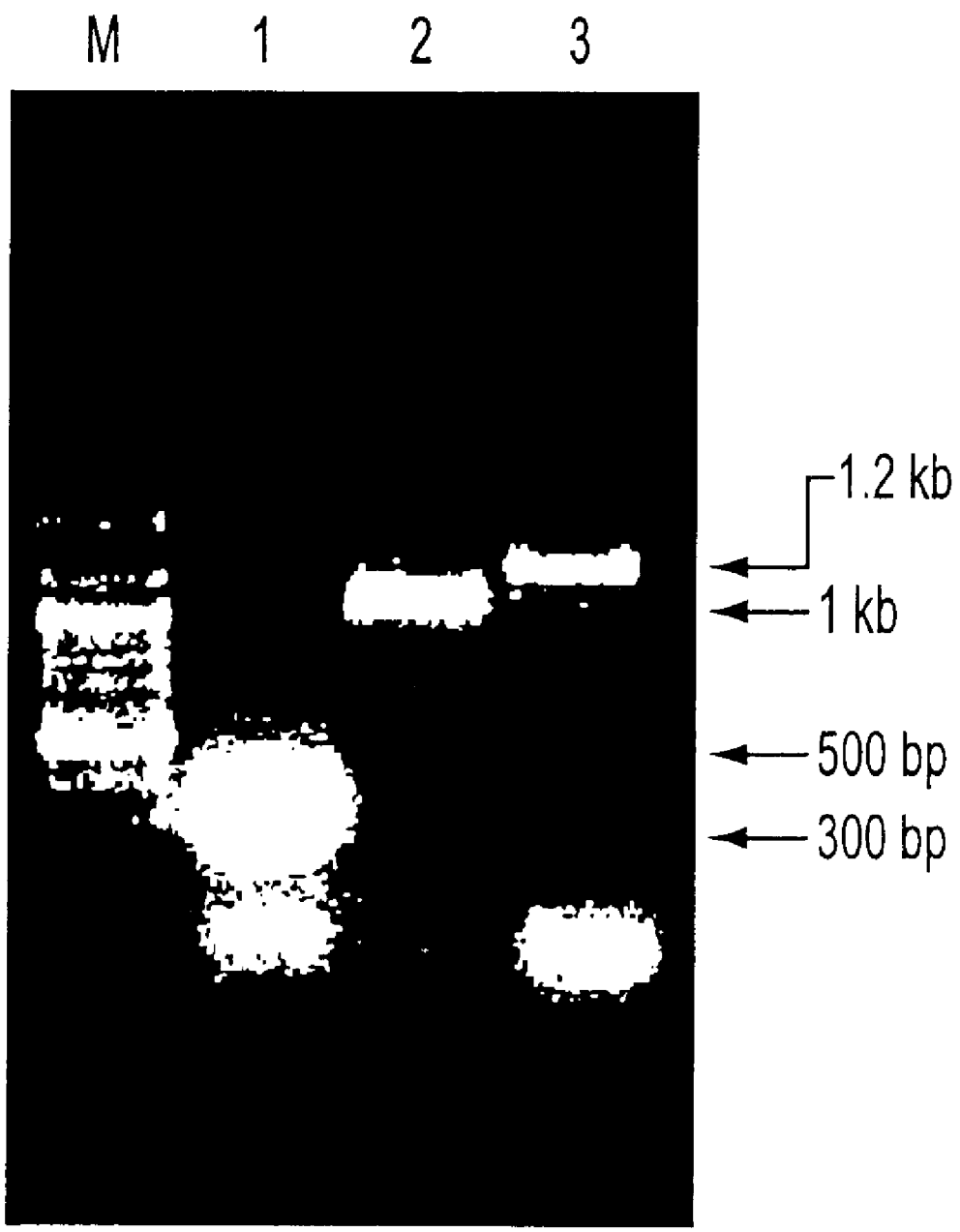
FIG. 1 represents the result of agarose gel electrophoresis of the products obtained by amplification of both ends of β-actin cDNA by the process and the primer of the present invention.

The object of the present invention is to provide a process for selective amplification of full-length cDNA. More particularly, the object of the present invention is to provide a process for selective amplification of full-length cDNA, which comprises: i) a step for preparing a hybrid composed mRNA strand and cDNA strand of which three (3) or four (4) dCMPs are combined at 3' end by treating mRNA with reverse transcription; separately from the above step, ii) a step for adenylating single strand anchor of which biotin or phosphate group is combined at 3' end and phosphate group is combined at 5' end; iii) a step for ligating said adenylated single strand anchor selectively to 3' end of full-length cDNA strand of said cDNA/mRNA hybrid to select full-length cDNA/mRNA hybrid; and iv) a step for amplifying only full-length cDNA strand through PCR which employs a primer of which base sequence is complementary to that of said anchor.

The another object of the present invention is to provide a process for selective amplification of a specific part of cDNA or mRNA, which comprises: i) a step for preparing a hybrid composed of mRNA strand and cDNA strand of which three (3) or four (4) dCMPs are combined at 3' end by treating mRNA with reverse transcription; separately from the above step, ii) a step for adenylating single strand anchor of which biotin or phosphate group is combined at 3' end and phosphate group is combined at 5' end; iii) a step for ligating said adenylated single strand anchor selectively to 3' end of cDNA strand of said cDNA/mRNA hybrid to select full-length cDNA/mRNA hybrid; and iv) a step for selectively amplifying a part of full-length cDNA strand through PCR which employs a gene-specific primer of which base sequence is complementary to that of target genes.

The still another object of the present invention is to provide a process for preparation of full-length cDNA in large scale through gene-cloning, which comprises: i) a step for preparing a hybrid composed of mRNA strand and cDNA strand of which three (3) or four (4) dCMPa are combined at 3' end by treating mRNA with reverse transcription; separately from the above step, ii) a step for adenylating single strand anchor of which biotin or phosphate group is combined at 3' end and phosphate group is combined at 5' end; iii) a step for ligating said adenylated single strand anchor selectively to 3' end of cDNA strand of said cDNA/mRNA hybrid to select full-length cDNA/ mRNA hybrid; iv) a step for amplifying only the full-length cDNA strand through PCR which employs a primer of which base sequence is complementary to that of said anchor; v) a step for making double strand cDNA which has specific cohesive ends, by cleaving the specific site of said anchor ligated on full-length cDNA prepared through the above step i) with restriction enzyme; vi) a step for inserting said double strand cDNA containing cohesive ends into a vector by using DNA ligase; vii) a step for transforming the vector which contains said cDNA into host cells; viii) a step for cloning said host cells in large scale; and ix) a step for separating the full-length cDNA from the vector obtained from said host cells, by cleaving full-length cDNA from said vector with DNA restriction enzyme which is used in step v).

Reverse transcriptase (RTase) used herein is M-MLV, which is a kind of terminal transferase capable of adding three (3) or four (4) dCMPs to 3' end of the cDNA by recognizing 5' cap structure of mRNA. More information about RTase is described in "Nucleic acids Research, 1999, vol, 27, No 21, e31" of Schmidt and Mueller in detail.

The RNA ligase used herein is T4 RNA ligase which can recognize trinucleosidediphosphate (NpNpNOH) as a minimum substrate for a phosphate acceptor and also recognize nucleoside 3',5'-biphosphate group (pNp) as a minimum substrate for a phosphate donor.

Therefore, only primary full-length cDNA containing three or more template-independent cytosine residues, can be ligated to other oligomers by T4 RNA ligase. However, cDNA containing two or less dNTPs at its 3' end, cannot be ligated to other oligomers since two or less dNTPs cannot be recognized by T4 RNA ligase.

That is, only the primary full-length cDNA containing three or more dCMPs at its 3' end, which was added through template-independent reaction by RTase, can be recognized by T4 RNA ligase during the primary cDNA synthesis.

Optionally, the process of the present invention may further comprise an additional step between step iii) and step iv) for removing the residual mRNA without participating in cDNA synthesis, by using ribonuclease such as RNase A.

A single strand anchor of which biotin or phosphate group is combined at 3' end and phosphate group is combined at 5' end to be ligated with another single strand, is prepared through the process of the present invention; and the single strand anchor thus prepared is ligated to 3' end of full-length cDNA wherein three (3) or four (4) cytosine residues are combined, by treating RNA ligase such as T4 RNA ligase; and the cDNA thus selected is amplified through PCR by using a anchor-specific primer.

Through the process of the present invention, double strand cDNA can be completely amplified by PCR wherein the above primer and CapFish(dT) primer are employed to produce cDNA library.

The time required for the process of the present invention is shorter than that of the conventional process since the additional step for treatment of terminal transferase is not required for the process of the present invention.

More than eight (8) hours is required for ligation between the anchor and nucleic acid for the best yield of the process of the present invention. However, the pre-adenylated anchor which contains phosphate group, can be ligated with nucleic acid within three (3) hours. Consequently, the reaction time required for full-length cDNA selection which should be repeated for several times, can be shortened and thereby, whole reaction time can be reduced.

The pre-adenylated anchor thus prepared, is so stable that it can be stored at room temperature for several weeks. Three (3) hours of ligation time is sufficient to ligate pre-adenylated anchor to nucleic acid with high yield, whereas more than eight (8) hours of ligation time is required for obtaining the sufficient amount of template strands sufficient to be amplified.

The process of the present invention is less complicated than "Capselect" method since the step for treatment of terminal transferase can be omitted.

Hereinafter, the present invention will be described in greater detail with reference to the following examples. The examples are given only for illustration of the present invention and not to be limiting the present invention.

EXAMPLE 1

Selection of Full-Length cDNA and Amplification of 5' End Region of the Full-Length cDNA The cDNA of TFR mRNA which exists in small amount in cell, and the cDNA of β-actin mRNA and the cDNA of GAPDH mRNA which exist in large amount in cell, were selected from the cDNAs prepared through reverse transcription by using 2 μg of total RNAs or 100 ng of total mRNA. Then, the cDNAs thus prepared were amplified through the following process of the present invention.

1-1: Synthesis of cDNA Strand

Total RNA was extracted from tissue of human placenta, spleen and liver by using Blood RNA PrepMate™ (Bioneer, Korea). Messenger RNA was extracted by using dT celluose column, if needed.

2 μg of total RNA or 100 ng of mRNA was used to synthesize cDNA strand by using oligo(dT) anchor primer [CapFish(dT)]. 20 μl of the reaction mixture for reverse transcription, which contains 50 mM Tris-HCl pH 8.3, 75 mM KCl, 6 mM $MgCl_2$, 10 mM DTT, 1 mM dNTPs each and 1 μl of PowerScript™ RTase (Clontech, U.S.A.), was incubated for one (1) hour at 42° C. This reaction mixture for reverse transcription was described in U.S. Pat. No. 4,943,531 in detail. 0.4 μl of 100 mM $MnCl_2$ was added to the reaction mixture, if needed. Then the reaction mixture was incubated for 30 min. at 420° C. To make reaction mixture, volume was 100 μl, $ddH_2O$ was added and then it was extracted by using phenol-chloroform. Then, 10 μl of 3M sodium acetate/DEPC and 200 μl of absolute ethanol were added into the reaction mixture to precipitate RNA and cDNA/mRNA hybrid.

1-2: Synthesis of Anchor and Ligation Between the Anchor and Nucleic Acid by T4 RNA Ligase 300 pmole of the anchor (CapFishLink) was incubated with 50 mM Tris-HCl pH 7.5, 10 mM $MgCl_2$, 10 M DTT, 1 mM ATP, 10 μl of 25% PEG 6000, 10% DMSO, 0.006% BSA and 30 unit of T4 RNA ligaseF (Takara, Japan) for twelve (12) hours at 37° C. without using RNA and cDNA/mRNA hybrid obtained in Example 1-1.

60 pmole of the anchor prepared in the above step, was added to the reaction mixture containing RNA and cDNA/mRNA hybrid obtained in Example 1-1. Then, the reaction mixture was treated with 10 unit of T4 RNA ligase for three (3) hours at 37° C. RNAs which had not been participated in cDNA synthesis, were removed by using 4 μl of 10 mg/ml RNase for 30 min. at 37° C.

1-3: Amplification Through PCR

1 μl of the reaction mixture prepared in Example 1-2, was used as a template to amplify 3' end region and 5' end region of β-actin mRNA through RACE (rapid amplification of cDNA end).

The anchor-specific primer (CapFishRaceN 1 and 2) and the anti-sense primer (β-ActinR) of β-actin mRNA (Genebank accession No: NM_001101), were used to amplify 5' end region of β-actin mRNA through 5'-end RACE. The CapFish(dT) and the sense-primer of β-actin mRNA were used to amplify 3' end region of β-actin mRNA through 3'-RACE. The condition for PCR such as the 3'-RACE and the 5'-RACE of the present invention, was as follows:

The polymerase chain reaction was initiated for 5 min. at 94° C., and was carried out for 1 min. at 94° C., for 2 min. at 60° C. and then, for 3 min. at 72° C. The above steps were repeated five (5) times.

Then, supplemental reaction was carried out for 1 min. at 94° C., for 1 min. 58° C. and for 2 min. at 72° C. Such supplementary reaction was repeated thirty (30) times. Then, final amplification reaction was carried out for 5 min. at 72° C. The result was represented in FIG. 1.

In FIG. 1, M represents the size marker. Lane 1 represents the result of agarose gel-electrophoresis of the β-actin cDNA amplified through PCR which employs β-actin sense-primer and β-actin anti-sense primer. Lane 2 represents the result of agarose gel-electrophoresis of the 3' end region of β-actin cDNA amplified through 3'-RACE by using CapFish(dT) primer and β-actin sense-primer. Lane 3 represents the result of agarose gel-electrophoresis of the 5' end region of β-actin cDNA amplified through 5'-RACE by using CapFishRace1 primer and β-actin anti-sense primer.

The primer for GAPDH gene (Genebank accession No: M33197), the primer for RNA polymerase II gene and the primer for TFR gene (Genebank accession No: X01060), together with CapFishRace1 primer, were employed for amplification of the 5' end region of each cDNA through 5'-RACE.

Figure 3:
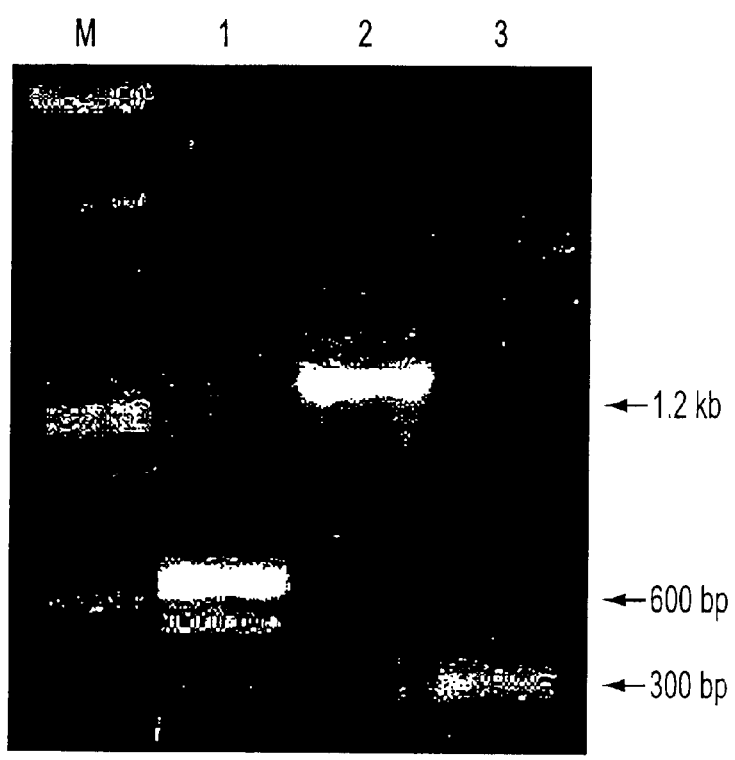
FIG. 3 represents the result of agarose gel electrophoresis of the products obtained by the amplification of GAPDH (Lane1), Y-actin (Lane 2), RNA polymerase II (Lane3) prepared from 2 μg of total spleen mRNA by using the process and the primer of the present invention.

As represented in FIG. 3, 5' end region of GAPDH gene and β-actin gene which exist sufficiently in cell, and 5' end region of RNA polymerase and TFR gene which exist in medium or small amount in cell, could be amplified through one (1) round of 5'-RACE by using 100 ng of each mRNA.

5' end region of GAPDH, 5' end region of β-actin and 5' end region of RNA polymerase could be amplified through one (1) round of 5'-RACE by using total RNA.

1-4: Determination of Sequence for Product of Reverse Transcription

The cDNA amplified through PCR in which AccuPrep™ gel purification kit (Bioneer, Korea) was employed, was purified and cloned. Then, the reaction for determination of sequence of the cDNA was carried out by using AccuPrep™ DNA sequencing kit (Bioneer, Korea). Then, the resulting reaction mixture was applied on 4% denaturing gel and detected with Silverstar™ staining kit (Bioneer, Korea) to determine their base sequences.

Figure 4:
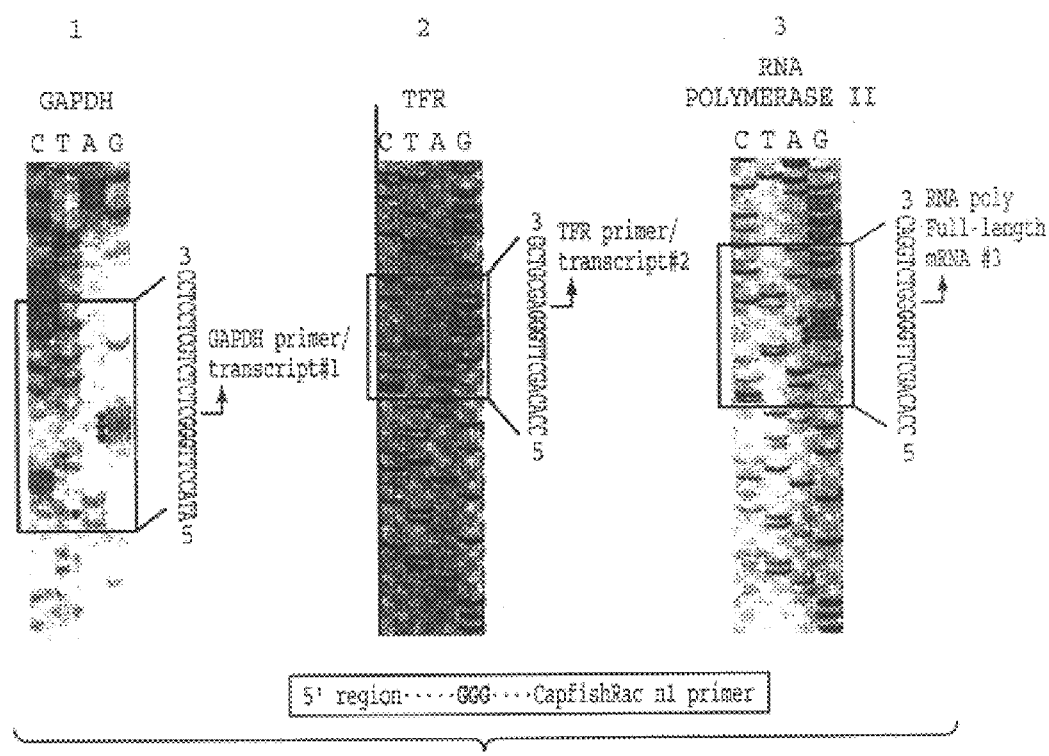
FIG. 4 represents the result of analysis wherein the base sequences determined by amplifying 5' end of full-length GAPDH(FIG. 4-1) (SEQ ID NO: 13), full-length TFR(FIG. 4-2) (SEQ ID NO: 14), and full-length RNA polymerase II(FIG. 4-3) (SEQ ID NO: 15) by using the process and the primer of the present invention, and then cloning them, are compared with the full-length sequences which have been reported previously.

As represented in FIG. 4, the base sequences of 5' end region of GAPDH gene (Genebank accession No: J04038), 5' end region of RNA polymerase II gene (Genebank accession No: X984331.1) and 5' end region of TFR gene (Genebank accession No: X04664), were corresponded to their base sequences which had been reported previously.

The above result shows the specificity of the process of the present invention, which is capable of amplifying mRNA existing in small amount in cell such as TFR gene in case that 100 ng of mRNA was used.

TABLE 1 base sequences of primer and anchor employed

| | Base sequence | |
|---|---|---|
| Cap FishLink | 5'phosphate-AAGDAGTGGTATCAACGAGTGCGGCCGCGGG-biotin3' | (SEQ ID NO: 1) |
| CapFish (dT) | 5' ATTCTAGAGCGGCCGCGACATGT (30) VN 3' | (SEQ ID NO: 2) |
| CapFishRace1 | 5' CCCGCGGCCGCACTCGTTGATACCACTGCTTGGG 3' | (SEQ ID NO: 3) |
| CapFishRace2 | 5' CCCGCGGCCGCACTCGTTGATACCACTGCTTGGGG 3' | (SEQ ID NO: 4) |
| CapFishRaceN1 | 5' CGCACTCGTTGATACCACTGCTTGGG 3' | (SEQ ID NO: 5) |
| CapFishRaceN2 | 5' CGCACTCGTTGATACCACTGCTTGGGG 3' | (SEQ ID NO: 6) |

TABLE 1-continued base sequences of primer and anchor employed

| | Base sequence | |
|---|---|---|
| β-acticF | 5' GCCCTGAGGCACTCTTCCAGCCTTCCTTCC 3' | (SEQ ID NO: 7) |
| β-actinR | 5' GTCATACTCCTGCTTGCTGATCCACATCTG 3' | (SEQ ID NO: 8) |
| GAPDHF | 5' GTGGCGTATAGTAAGGCTGCAACAGTTACT 3' | (SEQ ID NO: 9) |
| GAPDHR | 5' AAGCAGTTGGTGGTGCAGGAGGCATTGCTG 3' | (SEQ ID NO: 10) |
| RNApol IIR | 5' CACTGATGAGGTCGGTGATGGCGTTGGTAA 3' | (SEQ ID NO: 11) |
| TFRR | 5' TGCTGGTACCAAGAACCGCTTTATCCAGAT 3' | (SEQ ID NO: 12) |

FIG. 1 represents the result of agarose gel electrophoresis of the products obtained by amplification of both ends of β-actin cDNA by the process and the primer of the present invention.

Lane 1 is the result of amplification in which sense primer and anti-sense primer were employed. Lane 2 and Lane 3 are the result of amplification of 3' end region and 5' end region of β-actin cDNA respectively, in which the sense and anti-sense gene-specific primer and the anchor-specific primer were employed. The length of all products corresponds to the length derived from the full-length β-actin gene which had been reported previously.

Figure 2:
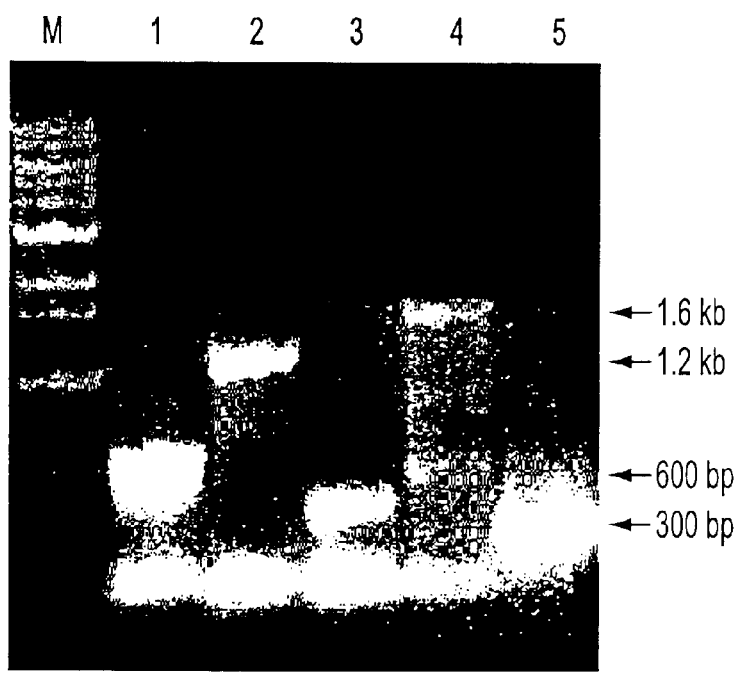
FIG. 2 represents the result of agarose gel electrophoresis of the products obtained by the amplification of 5' end of full-length GAPDH (Lane1), full-length β-actin (Lane2), full-length RNA polymerase II (Lane3) and full-length TFR (Lane4) prepared from 100 ng of mRNA by using the process and primer of the present invention.

FIG. 2 represents the result of agarose gel electrophoresis of the products obtained by amplification of 5' end region of full-length GAPDH (Lane 1), 5' end region of full-length β-actin (Lane 2), 5' end region of full-length of RNA polymerase II (Lane 3) and 5' end region of full-length TFR (Lane 4) through the process and the primer of the present invention by using 100 ng of mRNA. Lane 5 is the result of agarose gel electrophoresis of the product (300 bp) of a portion of GAPDH gene, which was amplified by using sense and anti-sense primer.

FIG. 3 represents the result of agarose gel electrophoresis of the products obtained by the amplification of GAPDH (Lane 1), Y-actin (Lane 2), RNA polymerase II (Lane 3) prepared from 2 μg of total spleen mRNA by using the process and the primer of the present invention.

FIG. 4 represents the result of sequence analysis in which the base sequences determined by amplifying 5' end of full-length GAPDH gene (FIG. 4-1), 5' end of full-length TFR gene (FIG. 4-2) and 5' end of full-length RNA polymerase II gene (FIG. 4-3) by using the process and the primer of the present invention, and then by cloning them, were compared with their full-length sequences which had been reported previously.

Figure 5:
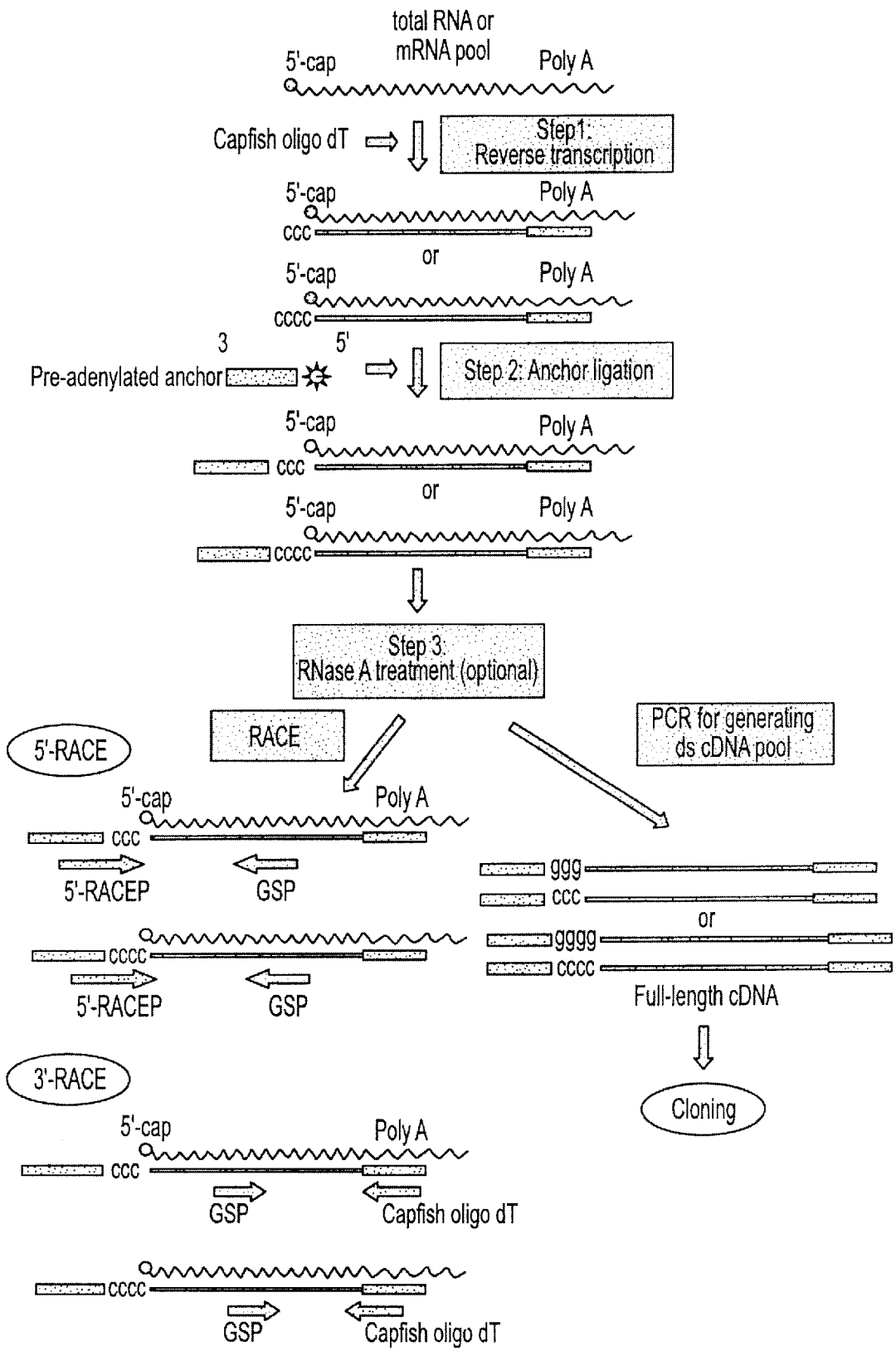
FIG. 5 represents the brief process of the present invention for preparing full-length cDNA.

FIG. 5 represents the brief process of the present invention for the preparation of full-length cDNA.

INDUSTRIAL APPLICABILITY

The process of the present invention is more efficient and simple process than conventional process to prepare full-length cDNA since the process of the present invention requires only two steps for preparation of full-length cDNA; one is a step for reverse transcription for synthesis of cDNA from mRNA and the other is a step for ligation between pre-adenylated anchor and the full-length cDNA. Consequently, whole reaction time for selective amplification of full-length cDNA, can be shortened.

Gene cloning required to construct cDNA library, can be carried out more easily through the process of the present invention than conventional process since there is a recognition site for specific restriction enzyme such as NotI, SmaI, XbaI, BglII, XhoI, SalI at Capfish primer of the present invention.

In addition, ligation between the anchor and full-length cDNA can be carried out more easily through the process of the present invention than conventional process since the anchor is adenylated previously.

Therefore, full-length cDNA which can provide important information to reveal structure of a gene and the function thereof, can be amplified more easily and efficiently through the process of the present invention than conventional process.

While the present invention has been particularly shown and described with reference to particular embodiments thereof, it will be understood by those skilled in the art that various changes in form and details may be effected therein without departing from the spirit and scope of the invention as defined by the appended claims.

This application claims priority from the Korean Patent Application No. KR 10-2001-0022956, the contents of which are hereby incorporated by reference in their entirety, including the specification, drawings and claims.

What is claimed is:

1. A process for selective amplification of a full-length cDNA, which comprises:
   i) preparing a hybrid comprising an mRNA strand and a cDNA strand having three (3) or four (4) dCMPs at 3' end by treating said mRNA with reverse transcriptase;
   ii) adenylating a single strand anchor having a biotin or phosphate group at 3' end and a phosphate group at 5' end;
   iii) ligating, using RNA ligase, an adenylated single strand anchor obtained from step (ii) selectively to 3' end of a full-length cDNA strand in a cDNA/mRNA hybrid obtained from step (i) to select a full-length cDNA/mRNA hybrid; and
   iv) amplifying only said full-length cDNA strand through polymerase chain reaction by using a primer having a base sequence is complementary to that of said anchor.

2. The process according to claim 1, wherein said reverse transcriptase is M-MLV.

3. The process according to claim 1, wherein said RNA ligase is T4 RNA ligase.

4. The process according to claim 1, which further comprises between step iii) and step iv):
   a step for removing the residual single strand mRNA by using ribonuclease.

5. A process for selective amplification of a part of cDNA or mRNA, which comprises:
   i) preparing a hybrid comprising an mRNA strand and a cDNA strand having three(3) or four(4) dCMPs at 3' end by treating said mRNA with reverse transcriptase;
   ii) adenylating a single strand anchor having a biotin or phosphate group at 3' end and a phosphate at 5' end;
   iii) ligating, using RNA ligase, an adenylated single strand anchor obtained from step (ii) selectively to 3' end of said cDNA strand of a cDNA/mRNA hybrid obtained from step (i) to select full-length cDNA/mRNA hybrid; and
   iv) amplifying selectively a part of said full-length cDNA strand through polymerase chain reaction by using a gene-specific primer having a base sequence that is complementary to that of a target gene.

6. A process for preparing a full-length cDNA, which comprises:
   i) preparing a hybrid comprising an mRNA strand and a cDNA strand having three(3) or four(4) dCMPs at 3' end by treating said mRNA with reverse transcriptase;
   ii) adenylating a single strand anchor having a biotin or phosphate group at 3' end and a phosphate group at 5' end;
   iii) ligating, using RNA ligase, an adenylated single strand anchor obtained from step (ii) selectively to 3' end of said cDNA strand of a cDNA/mRNA hybrid obtained from step (i) to select a full-length cDNA/mRNA hybrid;
   iv) amplifying only said full-length cDNA strand through polymerase chain reaction by using a primer having a base sequence that is complementary to that of said anchor;
   v) preparing a double strand cDNA that has specific cohesive ends, by cleaving a specific site of said anchor ligated to said full-length cDNA obtained from step (iv), using restriction enzyme;
   vi) inserting said double strand cDNA containing a cohesive end into a vector using DNA ligase;
   vii) transforming said vector containing said cDNA into a host cell;
   viii) cloning said host cell in a large scale; and
   ix) separating said full-length cDNA from said host cells, by cleaving said full-length cDNA from said vector with the restriction enzyme used in step v).

7. The process according to claim 5, wherein said reverse transcriptase is M-MLV.

8. The process according to claim 5, wherein said RNA ligase is T4 RNA ligase.

9. The process according to claim 5, further comprising between step iii) and step iv):
   the step for removing a residual single strand mRNA by using ribonuclease.

10. The process according to claim 9, wherein said ribonuclease is ribonuclease A (RNase A).

11. The process according to claim 6, wherein said reverse transcriptase is M-MLV.

12. The process according to claim 6, wherein said RNA ligase is T4 RNA ligase.

13. The process according to claim 6, further comprising a step for ligating an adenine group to said anchor.

14. The process according to claim 6, further comprises between step iii) and step iv):
   the step for removing a residual single strand mRNA using ribonuclease.

15. The process according to claim 14, wherein said ribonuclease is RNase A.

16. A process for obtaining a full-length cDNA, which comprises:
   i) preparing a hybrid of an mRNA strand and a cDNA strand having three (3) or four (4) dCMPs at 3' end by treating mRNA with reverse transcriptase;
   ii) adenylating a single strand anchor having a biotin or phosphate group at 3' end and a phosphate group at 5' end; and
   iii) ligating selectively said single strand anchor to 3' end of said cDNA strand of a full-length cDNA/mRNA hybrid to select a full-length cDNA/mRNA hybrid.

* * * * *

SEQUENCE LISTING

<160> NUMBER OF SEQ ID NOS: 15

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1

```
aagdagtggt atcaacgagt gcggccgcgg g                           31
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2

```
attctagagc ggccgcgaca tgt                                    23
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 3

```
cccgcggccg cactcgttga taccactgct tggg                        34
```

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 4

```
cccgcggccg cactcgttga taccactgct tgggg                       35
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 5

```
cgcactcgtt gataccactg cttggg                                 26
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6

```
cgcactcgtt gataccactg cttgggg                                27
```

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7

```
gccctgaggc actcttccag ccttccttcc                             30
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
gtcatactcc tgcttgctga tccacatctg          30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gtggcgtata gtaaggctgc aacagttact          30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
aagcagttgg tggtgcagga ggcattgctg          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
cactgatgag gtcggtgatg gcgttggtaa          30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
tgctggtacc aagaaccgct ttatccagat          30

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
ataccttggg ctctctgctc ctcc          24

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 14
ccacagcttg ggagcgtcg          19

```
-continued

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 15
ccacagcttg ggggtctgga c                                              21
```